United States Patent [19]
Inukai et al.

[11] Patent Number: 5,776,071
[45] Date of Patent: Jul. 7, 1998

[54] BLOOD PRESSURE MONITOR APPARATUS

[75] Inventors: Hidekatsu Inukai, Nagoya; Toshihiko Ogura, Inuyama, both of Japan

[73] Assignee: Colin Corporation, Komaki, Japan

[21] Appl. No.: 845,478

[22] Filed: Apr. 25, 1997

[30] Foreign Application Priority Data

May 2, 1996 [JP] Japan ................... 8-111590

[51] Int. Cl.$^6$ ................................................. A61B 5/00
[52] U.S. Cl. .................. 600/493; 600/494; 600/500; 600/485
[58] Field of Search .................. 600/483, 485, 600/493–496, 500–503

[56] References Cited

U.S. PATENT DOCUMENTS

| | | | |
|---|---|---|---|
| 4,669,485 | 6/1987 | Russell | 600/493 |
| 4,889,133 | 12/1989 | Nelson et al. | 600/494 |
| 5,131,391 | 7/1992 | Sakai et al. | |
| 5,241,964 | 9/1993 | McQuilkin | 600/485 |
| 5,269,310 | 12/1993 | Jones et al. | 600/485 |
| 5,279,303 | 1/1994 | Kawamura et al. | 600/496 |
| 5,497,779 | 3/1996 | Takaya et al. | 600/485 |
| 5,533,511 | 7/1996 | Kaspari et al. | 600/500 |
| 5,590,649 | 1/1997 | Caro et al. | 600/500 |
| 5,649,543 | 7/1997 | Hosaka et al. | 600/500 |

FOREIGN PATENT DOCUMENTS

| | | |
|---|---|---|
| 0 123 313 A | 10/1984 | European Pat. Off. |
| A-2-177937 | 7/1990 | Japan |
| 557 671 A | 1/1975 | Switzerland |
| WO 92 03967 A | 3/1992 | WIPO |
| WO 96 11625 A | 4/1996 | WIPO |

*Primary Examiner*—Robert L. Nasser
*Attorney, Agent, or Firm*—Oliff & Berridge, PLC

[57] ABSTRACT

A blood pressure monitor apparatus including a blood pressure measuring device which includes a cuff and measures a blood pressure value of the subject by changing a pressing pressure of the cuff, a volume pulse wave detecting device which detects a volume pulse wave of the subject, a normalized pulse-wave area calculating device for successively calculating an area which is defined by a waveform of each of heartbeat-synchronous pulses of the volume pulse wave and is normalized based on a period and an amplitude of the each pulse of the volume pulse wave, a pulse wave area-blood pressure relationship determining device for determining a relationship between pulse-wave area and blood pressure, based on a normalized pulse-wave area value and a blood pressure value, when the blood pressure value is measured; and a monitor blood pressure determining device for successively determining a monitor blood-pressure value of the subject, based on each of normalized pulse-wave area values, according to the pulse wave area-blood pressure relationship.

11 Claims, 12 Drawing Sheets

BLOOD PRESSURE MONITOR APPARATUS

BACKGROUND OF THE INVENTION

1. Field of the invention

The present invention relates to a blood pressure monitor apparatus which monitors a blood pressure of a living subject based on each of heartbeat-synchronous pulses.

2. Related art statement

Generally, a blood pressure monitor apparatus which monitors a blood pressure of a living subject for a considerably long time includes a cuff being worn on a body portion of the subject and a blood pressure measuring device which periodically measures a blood pressure value of the subject by changing a pressing pressure of the cuff. The blood pressure values measured by the blood pressure measuring device enjoy high reliability.

However, in the above blood pressure monitor apparatus, if the interval between successive blood pressure measurements is shortened for improving the accuracy of blood pressure monitoring, the frequency of pressing of the cuff is increased and the subject feels more discomfort. In the case where the frequency of pressing of the cuff is excessively high, congestion occurs to the body portion of the subject, and accurate blood pressure values are not obtained.

Further, there has been proposed a blood pressure monitor apparatus including a blood pressure measuring device for measuring a blood pressure value of a living subject based on a variation of a pulse-synchronous wave obtained while a pressing pressure of a cuff is changed, a pressure pulse-wave sensor adapted to be pressed on an artery of the subject for detecting a pressure pulse wave produced from the artery of the subject, a pressure pulse wave-blood pressure relationship determining means for determining, at a predetermined period, a pressure pulse wave-blood pressure relationship between magnitude of pressure pulse wave and blood pressure, based on the pressure pulse wave detected by the pulse wave sensor and the blood pressure value measured by the blood pressure measuring device, by starting the blood pressure measuring device at the predetermined period, and a monitor blood pressure determining means for successively determining a monitor blood-pressure value based on an actual pressure pulse wave detected by the pressure pulse-wave sensor, according to the pressure pulse wave-blood pressure relationship. An example of the blood pressure monitor apparatus is disclosed in Laid-Open Publication No. 2-177937 of unexamined Japanese patent application. The blood pressure monitor apparatus is capable of determining a monitor blood-pressure value based on each of heartbeat-synchronous pulses, thereby performing the blood pressure monitor without any delay.

However, in the blood pressure monitor apparatus, it is needed to press the pressure pulse-wave sensor on the artery of the subject for detecting the pressure pulse-wave produced from the artery of the subject. To this end, the sensor has to be set on the skin of the subject right above the artery, such as the skin of a wrist. Therefore, the use of the sensor may be limited depending on the affected part of the subject. Further, in the case where the pressure pulse wave sensor is set with the help of a band, the pressure pulse-wave signal may be changed because the pressing state of the sensor may be changed due to, e.g., the body movement of the subject and accordingly an accurate blood pressure monitor may not be performed.

SUMMARY OF THE INVENTION

It is therefore an object of the present invention to provide a blood pressure monitor apparatus which accurately monitors a blood pressure of a living subject, without the problem of discomfort felt by the subject.

The inventors of the present invention have continued their study in the background of the above-described situation. They have found that a volume-pulse-wave area, e.g., photoelectric-pulse-wave area, indicative of a periodical change of blood volume in a peripheral portion of the subject changes in a close relation with a change of the blood-pressure values of the subject. The photoelectric pulse wave is obtained from a light reflected by, or transmitted through, a tissue of the subject when the light which has a wavelength capable of being reflected by hemoglobin present in blood of the tissue is emitted toward the tissue. The present invention has been developed based on this finding, whereby unnecessary blood pressure measurements using the cuff are avoided by monitoring the change of blood pressure based on the volume pulse-wave area.

The above object has been achieved by the present invention. According to a first aspect of the present invention, there is provided a blood pressure monitor apparatus comprising: (a) a blood pressure measuring device which includes a cuff adapted to be pressed on an artery of a living subject and measures a blood pressure value of the subject by changing a pressing pressure of the cuff; (b) a volume pulse wave detecting device which detects a volume pulse wave of the subject; (c) normalized pulse-wave area calculating means for successively calculating an area which is defined by a waveform of each of heartbeat-synchronous pulses of the volume pulse wave detected by the volume pulse wave detecting device and is normalized based on a period and an amplitude of the each pulse of the volume pulse wave; (d) pulse wave area-blood pressure relationship determining means for determining a relationship between pulse-wave area and blood pressure, based on a normalized pulse-wave area value calculated by the normalized pulse-wave area calculating means and a blood pressure value measured by the blood pressure measuring device, when the blood pressure value is measured; and (e) monitor blood pressure determining means for successively determining a monitor blood-pressure value of the subject, based on each of normalized pulse-wave area values successively calculated by the normalized pulse-wave area calculating means, according to the pulse wave area-blood pressure relationship determined by the pulse wave area-blood pressure relationship determining means.

In the above described blood pressure monitor apparatus, the pulse wave area-blood pressure relationship determining means determines a relationship between pulse-wave area and blood pressure, based on a normalized pulse-wave area value calculated by the normalized pulse-wave area calculating means and a blood pressure value measured by the blood pressure measuring device, when the blood pressure value is measured. The monitor blood pressure determining means successively determines a monitor blood-pressure value of the subject, based on each of normalized pulse-wave area values successively calculated by the normalized pulse-wave area calculating means, according to the pulse wave area-blood pressure relationship determined by the pulse wave area-blood pressure relationship determining means. Thus, the blood pressure monitor apparatus according to the present invention can obtain a monitor blood-pressure value based on each of heartbeat-synchronous pulses, so that the apparatus need not carry out the blood pressure measurements at an unnecessarily short interval for improving the accuracy of the blood pressure monitor operation. Thus, the frequency of pressing of the cuff is decreased and the distress of the subject is minimized. Additionally, the volume pulse-wave sensor can be easily worn on the subject. Since the signal detected by the sensor is not affected by the body movement of the subject or the like, the blood pressure monitor apparatus can continue the blood pressure monitor operation with accuracy.

According to a preferred feature of the first aspect of the invention, the monitor blood pressure apparatus further comprises monitor-blood-pressure abnormality judging means for judging whether each of the monitor-blood-pressure values successively determined by the monitor blood pressure determining means does not fall in a reference range, and controlling, when a negative judgment is made, the blood pressure measuring device to start a blood pressure measuring operation. In this case, when the negative judgment is made, the blood pressure measuring device starts a blood pressure measuring operation so as to update the pulse wave area-blood pressure relationship. Accordingly, the blood pressure monitor apparatus can automatically obtain the blood pressure value measured with higher reliability upon detection of the blood pressure abnormality and can raise the reliability of the monitor blood-pressure values obtained after the detection of the abnormality.

According to another feature of the first aspect of the invention, the blood pressure monitor apparatus further comprises an indicating device which indicates a trend graph of the monitor-blood-pressure values successively determined by the monitor blood pressure determining means. In this case, a medical person can easily recognize the change of the blood pressure and can accurately diagnose the blood pressure.

According to another feature of the first aspect of the invention, the indicating device comprises means for indicating that the negative judgement is made by the monitor-blood-pressure abnormality judging means. In this case, the medical person can easily recognize the monitor-blood-pressure abnormality and accurately grasp the condition of the subject or the operating state of the blood pressure monitor apparatus.

According to another feature of the first aspect of the invention, the volume pulse wave detecting device comprises a photoelectric pulse-wave sensor including a light-emitting and a light-receiving element, the light-emitting element emitting, toward a skin of the subject, a light having a wavelength which can be reflected by hemoglobin present in blood of the skin, the light-receiving element receiving the light scattered by the hemoglobin from the skin, the photoelectric pulse-wave sensor outputting a photoelectric pulse wave signal representing an instantaneous blood volume in capillaries of the skin. In this case, the light emitted from the light-emitting element may be a red or an infrared light.

According to another feature of the first aspect of the invention, the volume pulse wave detecting device comprises an impedance pulse-wave sensor including at least two electrodes being set on different locations of the skin of the subject at a predetermined interval, the impedance pulse-wave sensor outputting an impedance pulse-wave signal representing an instantaneous blood volume in a tissue of the skin located between said two electrodes.

According to a second aspect of the present invention, there is provided a blood pressure monitor apparatus including a blood pressure measuring device which includes a cuff being set on a body portion of a living subject and periodically measures a blood pressure value of the subject, based on a variation of a pulse wave produced while a pressing pressure of the cuff is changed, the blood pressure monitor apparatus comprising: (a) a volume pulse wave detecting device which detects a volume pulse wave of the subject; (b) normalized pulse-wave area calculating means for successively calculating an area which is defined by a waveform of each of heartbeat-synchronous pulses of the volume pulse wave detected by the volume pulse wave detecting device and is normalized based on a period and an amplitude of the each pulse of the volume pulse wave; (c) pulse-wave area change calculating means for calculating a change of the normalized pulse-wave area values successively calculated by the normalized pulse-wave area calculating means; and (d) blood-pressure change identifying means for identifying an abnormal blood-pressure change of the subject when the change of the normalized pulse-wave area values is greater than a reference value.

In the blood pressure monitor apparatus in accordance with the second aspect of the invention, the pulse-wave area change calculating means calculates a change of the normalized pulse-wave area values successively calculated by the normalized pulse-wave area calculating means. The blood-pressure change identifying means identifies an abnormal blood-pressure change of the subject when the change of the normalized pulse-wave area values is greater than the reference value. Thus, the blood pressure monitor apparatus can identify an abnormal blood-pressure change of the subject based on a change of the normalized pulse-wave area value calculated based on each of heartbeat-synchronous pulses, so that the apparatus need not carry out the blood pressure measurements at an unnecessarily short interval for improving the accuracy of the blood pressure monitor operation. Thus, the frequency of pressing of the cuff is decreased and the distress of the subject is minimized. Additionally, the volume pulse-wave sensor can be easily worn on the subject. Since the signal detected by the sensor is not affected by the body movement of the subject or the like, the blood pressure monitor apparatus can continue the blood pressure monitor operation with accuracy.

According to another feature of the second aspect of the invention, the blood-pressure change identifying means comprises means for controlling the blood pressure measuring device to start a blood pressure measuring operation upon identification of the abnormal blood-pressure change. In this case, when the abnormal blood-pressure change of the subject is identified, the blood pressure measuring device starts a blood pressure measuring operation using the cuff. Accordingly, the blood pressure monitor apparatus can automatically obtain the blood pressure value measured with higher reliability upon identification of the abnormal blood-pressure change.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
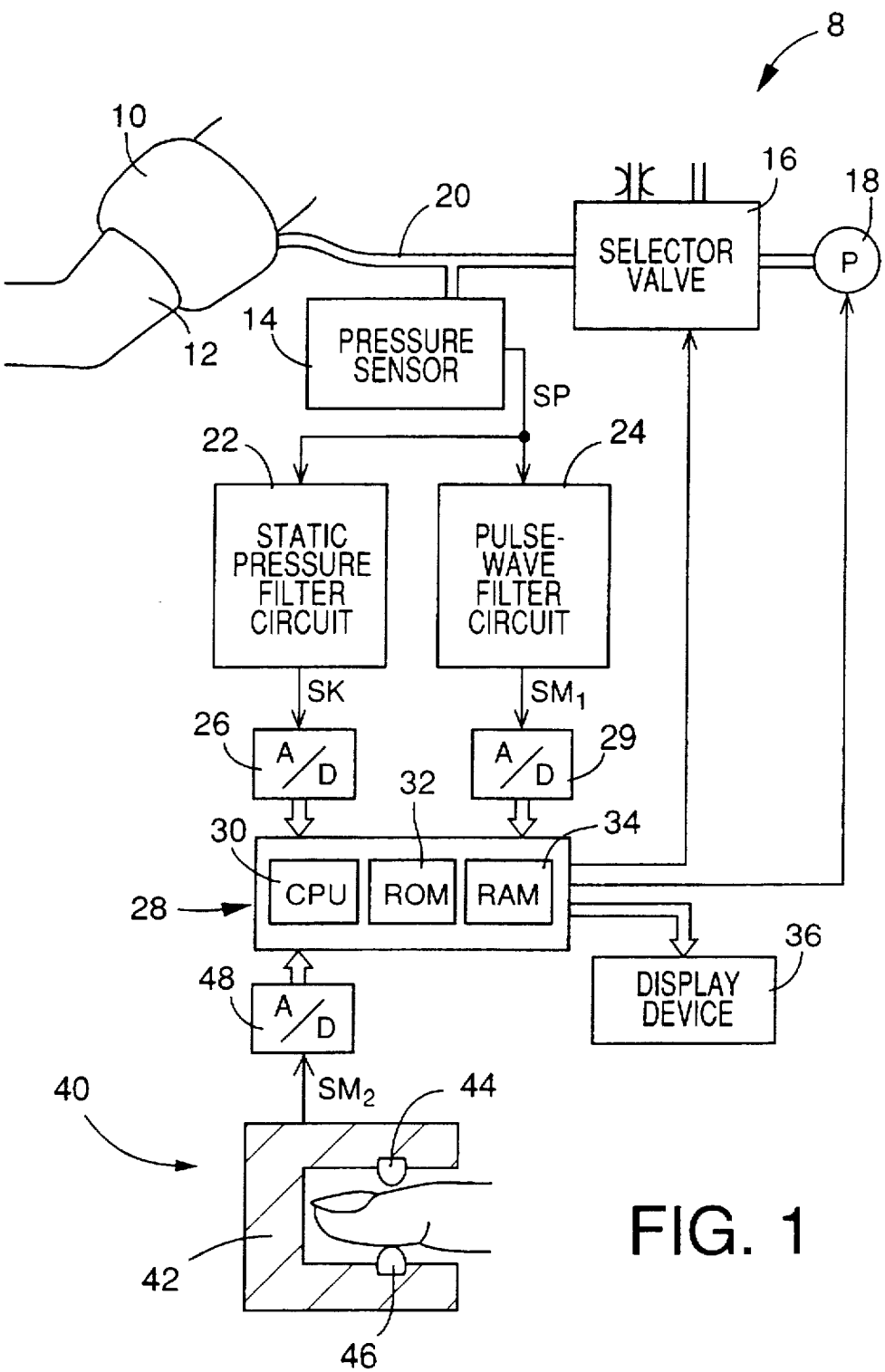
FIG. 1 is a diagrammatic view of a blood pressure monitor apparatus embodying the present invention.

Referring to FIG. 1, there will be described a blood pressure (BP) monitor apparatus 8 embodying the present invention.

In FIG. 1, the BP monitor apparatus 8 includes a cuff which has a belt-like cloth bag and a rubber bag accommodated in the cloth bag and which is adapted to be wound around an upper arm 12 of a patient, for example, and a pressure sensor 14, a selector valve 16 and an air pump 18 each of which is connected to the cuff 10 via a piping 20. The selector valve 16 is selectively placed in an inflation position in which the selector valve 16 permits a pressurized air to be supplied to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representative of the detected pressure to each of a static pressure filter circuit 22 and a pulse-wave filter circuit 24. The static pressure filter circuit 22 includes a low-pass filter and extracts, from the pressure signal SP, a static component contained in the signal SP, i.e., cuff pressure signal SK representative of the static cuff pressure $P_C$. The cuff pressure signal SK is supplied to an electronic control device 28 via an analog-to-digital (A/D) converter 26.

The pulse-wave filter circuit 24 includes a band-pass filter and extracts, from the pressure signal SP, an oscillating component having predetermined frequencies, i.e., pulse-wave signal $SM_1$. The pulse-wave signal $SM_1$ is supplied to the electronic control device 28 via an A/D converter 29. The pulse-wave signal $SM_1$ represents an oscillatory pressure wave which is produced from a brachial artery (not shown) of the patient in synchronism with the heartbeat of the patient and is propagated to the cuff 10. The cuff 10, the pressure sensor 14, and the pulse-wave filter circuit 24 cooperate with one another to function as a cuff pulse-wave sensor.

The electronic control device 28 is provided by a so-called microcomputer including a central processing unit (CPU) 30, a read only memory (ROM) 32, a random access memory (RAM) 34 and an input-and-output (I/O) port (not shown). The CPU 30 processes signals according to control programs pre-stored in the ROM 32 by utilizing a temporary-storage function of the RAM 34, supplies drive signals to the selector valve 16 and the air pump 18 through the I/O port, and outputs a display signal to a display device 36 through the I/O port.

The BP monitor apparatus 8 further includes a photoelectric pulse-wave sensor 40 which has a known construction. The photoelectric pulse-wave sensor 40 functions as a volume pulse-wave sensor. The sensor 40 includes a housing 42 which is capable of accommodating a body portion (e.g., finger) of a living subject therein. The housing 42 is provided with a light-emitting element 44 and a light-receiving element 46 which are opposed to each other on predetermined locations of an inner surface of the housing. The light-emitting element 44 emits, toward the finger of the subject, a red or an infrared light having a wavelength which can be reflected by hemoglobin present in blood of the finger, and the light-receiving element 46 receives the light transmitted through the finger. The sensor 40 outputs a photoelectric pulse wave signal $SM_2$ representative of an instantaneous amount of the hemoglobin, that is, instantaneous blood volume in the finger. The signal $SM_2$ oscillates or pulsates in synchronism with the heartbeat of the subject. The signal $SM_2$ is supplied to the control device 28 via an A/D converter 48.

Figure 2:
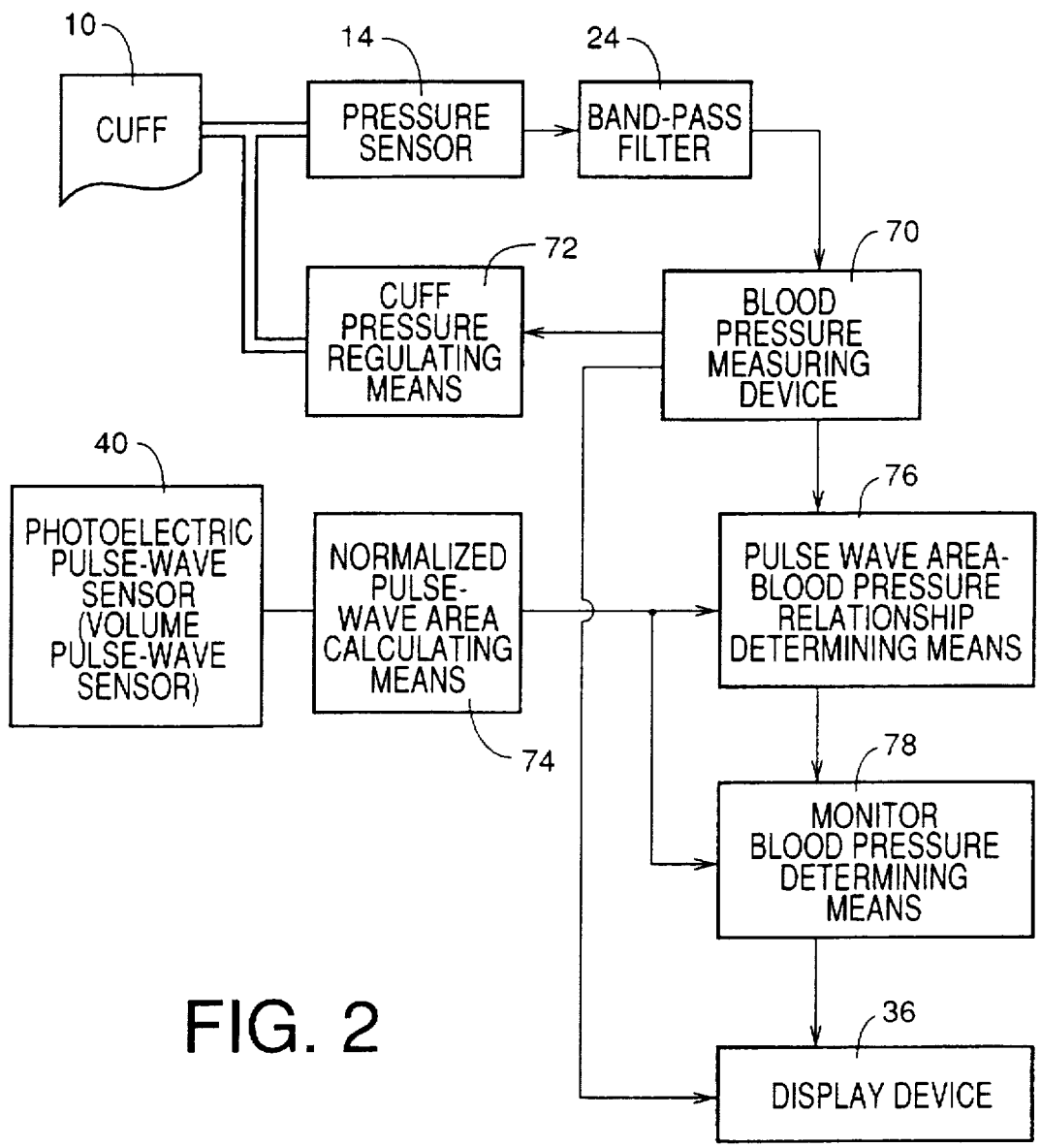
FIG. 2 is a block diagram for illustrating essential functions of an electronic control device of the apparatus of FIG. 1.

FIG. 2 illustrates essential functions of the electronic control device 28 of the present BP monitor apparatus 8. In the figure, a cuff pressure regulating means 72 changes a pressing pressure of the cuff 10 according to a well-known blood pressure measuring method during a blood pressure measurement of a blood pressure measuring device 70, which periodically starts a blood pressure measuring operation for calibrating pulse wave area-blood pressure relationship shown in FIG. 3. For example, the cuff pressure regulating means 72 increases the cuff pressure to a target value (e.g., 180 mmHg) which is greater than a systolic blood pressure value of the subject, and then slowly decreases it at the rate of about 3 mmHg/sec while a blood pressure measuring algorithm is carried out. Upon termination of the blood pressure measurement, the cuff pressure regulating means 72 releases the pressure of the cuff 10. The blood pressure measuring device 70 measures a systolic, a mean and a diastolic blood pressure value, $BP_{SYS}$, $BP_{MEAN}$, $BP_{DIA}$, of the patient, according to a well-known oscillometric method, based on a variation of respective magnitudes of heartbeat-synchronous pulses of the pulse-wave signal $SM_1$ obtained while the cuff pressure is slowly changed, and controls the display device 36 so as to indicate the measured blood pressure values.

Figure 4:
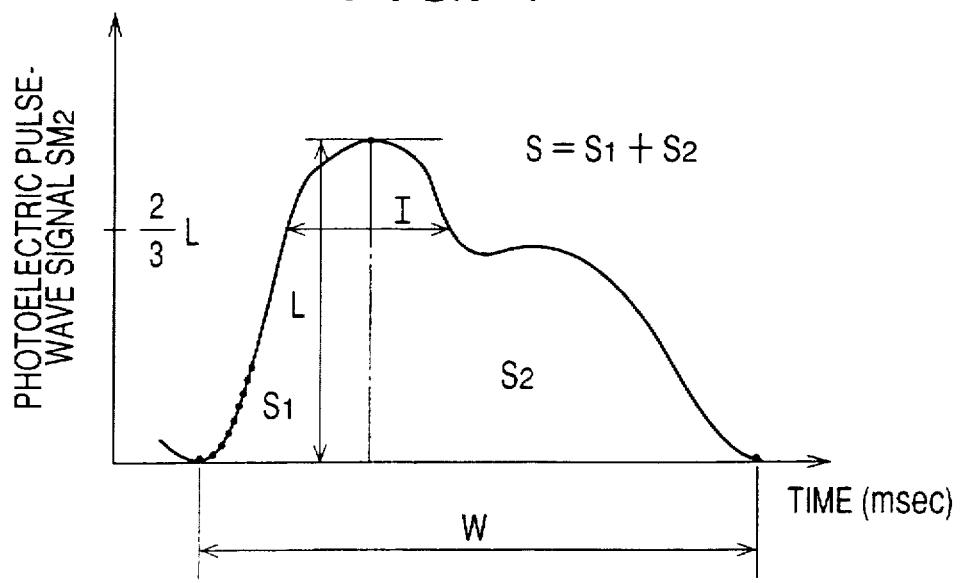
FIG. 4 is a view for illustrating a heartbeat-synchronous pulse of a photoelectric pulse wave detected by a photoelectric pulse-wave sensor of the apparatus of FIG. 1.

The photoelectric pulse-wave sensor 40 detects a photoelectric pulse wave from the finger of the subject which is accommodated in the housing 42 thereof and outputs the photoelectric pulse wave signal $SM_2$ representative of the detected photoelectric pulse wave. The photoelectric pulse-wave sensor 40 corresponds to the volume pulse-wave sensor. A normalized pulse-wave area calculating means 74 successively calculates an area $S_F$ which is defined by a waveform of each of heartbeat-synchronous pulses of the photoelectric pulse wave (or signal $SM_2$) and is normalized based on a period and an amplitude of the each pulse of the photoelectric pulse wave. More specifically, as shown in FIG. 4, the waveform of each pulse of the photoelectric pulse wave is defined by a series of data points indicative of respective magnitudes of the photoelectric pulse-wave signal $SM_2$ which are input to the control device 28 at a predetermined interval such as several milliseconds to several tens of milliseconds. A pulse-wave area S is obtained by integrating, in the period W of the pulse of the photoelectric pulse wave, the respective magnitudes of the pulse of the photoelectric pulse wave, and then the normalized pulse-wave area $S_F$ is calculated according to the following expression: $S_F=S/(W \times L)$. The normalized pulse-wave area $S_F$ is a dimensionless value indicative of a ratio of the pulse-wave area S to an area defined by the period W and the amplitude L of each pulse of the photoelectric pulse wave. In other cases, a symbol %MAP may be used in place of the symbol $S_F$.

Figure 3:
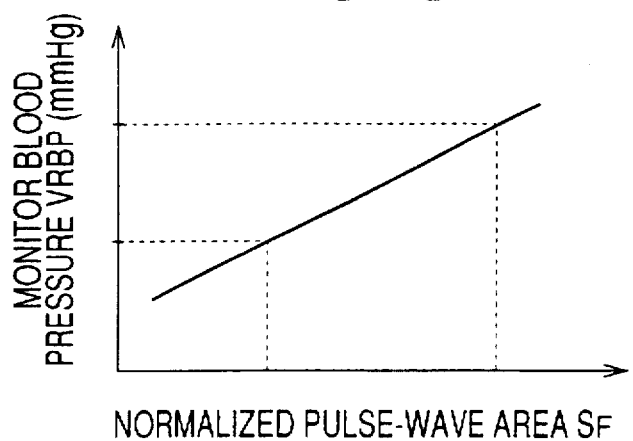
FIG. 3 is a graph showing a relationship between normalized pulse-wave area and monitor blood pressure, which is used on the apparatus of FIG. 1.

A pulse wave area-blood pressure relationship determining means 76 determines, in advance, a relationship between pulse-wave area and blood pressure, based on a normalized pulse-wave area value $S_F$ calculated by the normalized pulse-wave area calculating means 74 and a blood pressure value (one of a systolic, a mean, and a diastolic blood pressure value, $BP_{SYS}$, $BP_{MEAN}$, $BP_{DIA}$) measured by the blood pressure measuring device 70, when the blood pressure value is measured by the device 70. As shown in FIG. 3, the pulse wave area-blood pressure relationship is represented by, for example, an expression: $VRBP = \alpha \cdot S_F + \beta$, where $\alpha$ is a constant indicative of the slope, $\beta$ is a constant indicative of the intercept, and VRBP is a monitor blood-pressure value. The above expression $VRBP=f(S_F)$ may be determined based on one set of blood pressure value BP and normalized pulse-wave area value $S_F$, and a statistically obtained constant $\alpha$ or $\beta$ which is selected depending upon the sexuality and age of the subject. Alternatively, the expression $VRBP=f(S_F)$ may be determined based on at least two sets of blood pressure value BP and normalized pulse-wave area value $S_F$. In the latter case, the constants $\alpha$, $\beta$ in the expression are both determined as values for the specific subject. The one or two constants $\alpha$, $\beta$ in the expression is or are corrected each time a blood pressure measurement is carried out by the blood pressure measuring device 70.

A monitor blood pressure determining means 78 successively determines a monitor blood-pressure value VRBP of the subject, based on each of the normalized pulse-wave area values $S_F$ successively calculated by the normalized pulse-wave area calculating means 74, according to the expression $VRBP=f(S_F)$ determined by the pulse wave area-blood pressure relationship determining means 76, and controls the display device 36 to indicate a trend graph of the determined monitor blood-pressure values VRBP. In the case where one or more systolic blood pressure values $BP_{SYS}$ of the subject are used to determine the expression $VRBP=f(S_F)$, systolic monitor blood-pressure values are successively determined. Meanwhile, in the case where one or more mean blood pressure values $BP_{MEAN}$ are used to determine the expression, mean monitor blood-pressure values are successively determined; and in the case where one or more diastolic blood pressure values $BP_{DIA}$ are used to determine the expression, diastolic monitor blood-pressure values are successively determined.

Figure 5:
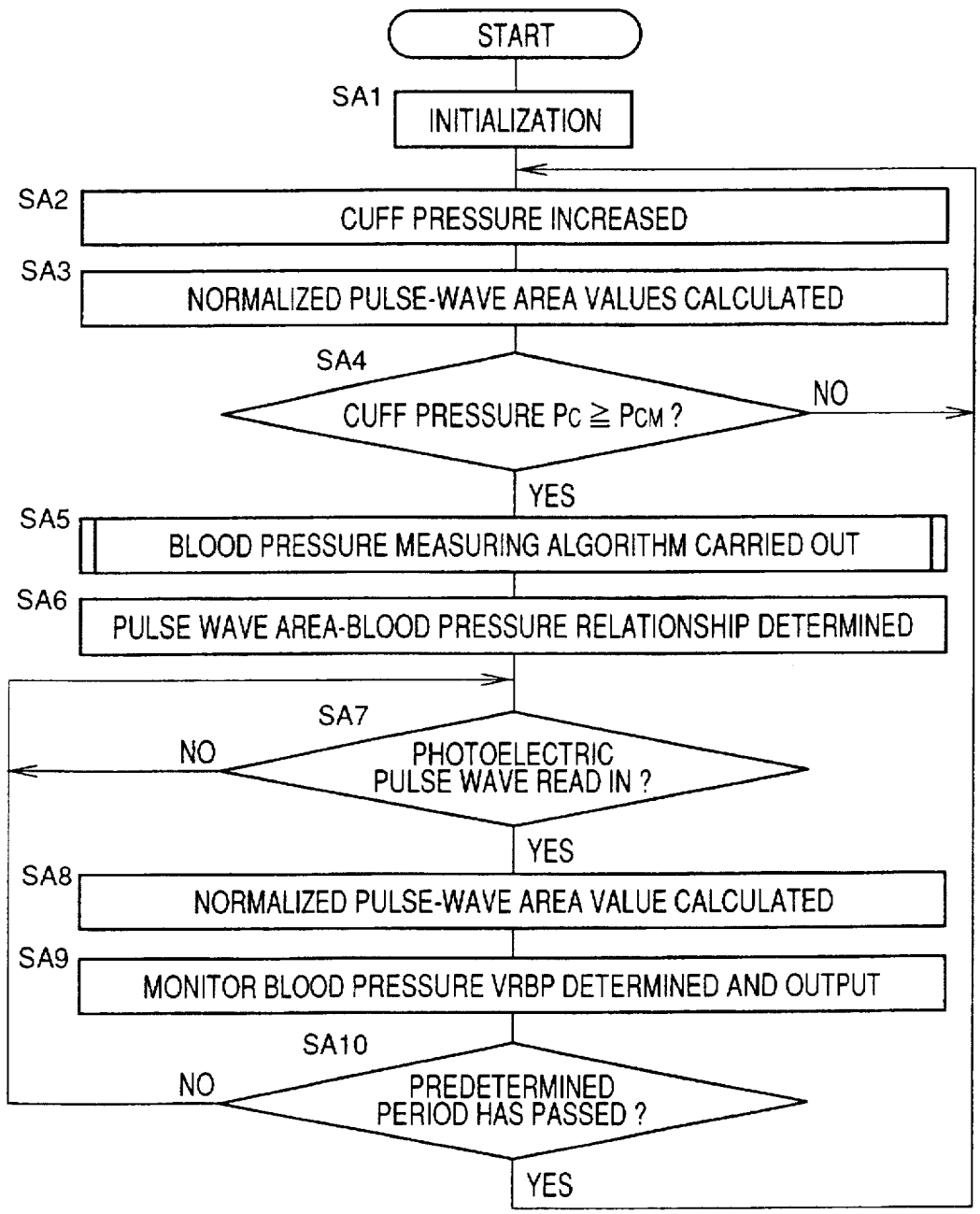
FIG. 5 is a flow chart representing the operation of the electronic control device of the apparatus of FIG. 1.

FIG. 5 is a flow chart representing an operation of the electronic control device 28 of the BP monitor apparatus 8. The control of the CPU 30 begins with Step SA1 of the flow chart of FIG. 5, where counters and registers (not shown) are reset. Step SA1 is followed by Step SA2 to quickly increase the cuff pressure for a blood pressure measurement, by switching the selector valve 16 to the inflation position and operating the air pump 18. Step SA2 corresponds to the cuff pressure regulating means 72.

The control of the CPU 30 goes to Step SA3 corresponding to the normalized pulse-wave area calculating means 74. At Step SA3, the CPU 30 successively obtains, based on the photoelectric pulse-wave signal $SM_2$ (shown in FIG. 4) detected by the photoelectric pulse-wave sensor 40, a pulse-wave area S $(=S_1+S_2)$ defined by a waveform of each of heartbeat-synchronous pulses of the photoelectric pulse wave, and calculates a normalized pulse-wave area $S_F$ based on a period W and an amplitude L of the each pulse of the photoelectric pulse wave, according to the expression $S_F=S/(W \times L)$.

Step SA3 is followed by Step SA4 to judge whether or not the cuff pressure $P_C$ is equal to or greater than a predetermined target value $P_{CM}$ (e.g., 180 mmHg). If a negative judgment is made at Step SA4, the control of the CPU 30 goes back to Step SA2 so as to continue the increasing of the cuff pressure $P_C$. On the other hand, if a positive judgment is made at Step SA4, the control of the CPU 30 goes to Step SA5 to carry out a blood pressure measuring algorithm. More specifically, the air pump 18 is stopped and the selector valve 16 is switched to the slow-deflation position where the selector valve 16 permits the pressurized air to be slowly discharged from the cuff 10. A systolic blood pressure $BP_{SYS}$, a mean blood pressure value $BP_{MEAN}$, and a diastolic blood pressure value $BP_{DIA}$ are determined, according to a well known oscillometric type blood pressure determining algorithm, based on a variation of respective amplitudes of pulses of the pulse wave represented by the pulse-wave signal $SM_1$ obtained while the cuff pressure is slowly decreased at a predetermined rate of 3 mmHg/sec, and a pulse rate is determined based on an interval of successive two pulses of the pulse wave. The thus measured blood pressure values and pulse rate are indicated on the display device 36, and then the selector valve 16 is switched to the quick-deflation position where the selector valve 16 permits the pressurized air to be quickly discharged from the cuff 10. Step SA5 corresponds to part of the blood pressure measuring device 70.

Step SA5 is followed by Step SA6 to determine a relationship between pulse-wave area and blood pressure, based on a normalized pulse-wave area values successively calculated at Step SA3 and a blood pressure value measured at Step SA5. More specifically, at Step SA6, the CPU 30 determines the relationship (the expression: $VRBP=\alpha \cdot S_F+\beta$) between pulse-wave area and blood pressure, based on an average of the normalized blood pressure values $S_F$ successively calculated at Step SA3 and one of the systolic, mean and diastolic blood pressure values, $BP_{SYS}$, $BP_{MEAN}$, $BP_{DIA}$ measured at Step SA5. Step SA6 corresponds to the pulse wave area-blood pressure relationship determining means 76.

Step SA6 is followed by Step SA7 to judge whether or not one pulse of the photoelectric pulse wave has been read in. If a negative judgment is made at Step SA7, the control of the CPU 30 waits until a positive judgment is made at Step SA7. If a positive judgment is made at Step SA7, the control of the CPU 30 goes to Step SA8 corresponding to the normalized pulse-wave area calculating means 74. At Step SA8, the CPU 30 calculates a normalized pulse-wave area $S_F$, based on the waveform of the one pulse of the photoelectric pulse wave read in at Step SA7 in the same manner as carried out at Step SA3.

Step SA8 is followed by Step SA9 to determine a monitor blood-pressure value VRBP based on the normalized pulse-wave area value $S_F$ calculated at Step SA8, according to the pulse wave area-blood pressure relationship (VRBP=α·$S_F$+β) determined at Step SA6, and then output the determined monitor blood-pressure value VRBP to the display device 36 so as to indicate a trend graph of the monitor blood-pressure values. Step SA9 corresponds to the monitor blood pressure determining means 78.

Then, the control of CPU 30 goes to Step SA10. At Step SA10, the CPU 30 judges whether or not a predetermined period (e.g., 15 to 20 minutes), that is, a calibration period, has passed after the prior blood pressure measurement was carried out at Step SA5. If a negative judgment is made at Step SA10, the control of the CPU 30 goes back to Step SA7 and the following steps so as to carry out one or more blood pressure monitor cycles, that is, successively determine a monitor blood-pressure value VRBP for each of heartbeat-synchronous pulses, and timewise indicate, on the display device 36, the trend graph of the determined monitor blood-pressure values VRBP as indicated at solid line in FIG. 6. On the other hand, if a positive judgment is made at Step SA10, the control of the CPU 30 goes back to Step SA2 and the following steps so as to determine a new pulse wave area-blood pressure relationship (VRBP=α·$S_F$+β).

In the above described embodiment, the pulse wave area-blood pressure relationship (VRBP=α$S_F$+β) between pulse-wave area and blood pressure is determined by the pulse wave area-blood pressure relationship determining means 76 (Step SA6), based on a normalized pulse-wave area $S_F$ calculated by the normalized pulse-wave area calculating means 74 (Step SA3) and one of blood pressure values $BP_{SYS}$, $BP_{MEAN}$, $BP_{DIA}$, measured by the blood pressure measuring device 70 (Step SA5), when the blood pressure values $BP_{SYS}$, $BP_{MEAN}$, $BP_{DIA}$ are measured. The monitor blood-pressure values VRBP are successively determined by the monitor blood pressure determining means 78 (Step SA9), based on the normalized pulse-wave area values $S_F$, successively obtained from the respective waveforms of heartbeat-synchronous pulses of the photoelectric pulse wave detected by the photoelectric pulse-wave sensor 40, according to the pulse wave area-blood pressure relationship determined by the pulse wave area-blood pressure relationship determining means 76. Thus, the BP monitor apparatus 8 can obtain a monitor blood-pressure value from each of heartbeat-synchronous pulses of the signal $SM_2$, so that the apparatus need not carry out the blood pressure measurements at an unnecessarily short interval for improving the accuracy of the blood pressure monitor operation. Thus, the frequency of pressing of the cuff is decreased and the distress of the subject is minimized. Additionally, the photoelectric pulse-wave sensor 40 can be easily worn on the subject. Since the signal $SM_2$ detected by the sensor 40 is not affected by the body movement of the subject or the like, the BP monitor apparatus 8 can continue the blood pressure monitor operation with accuracy.

In the above described embodiment, the normalized pulse-wave area $S_F$ is obtained by normalizing the pulse-wave area S defined by the waveform of each pulse of the photoelectric pulse wave, based on the period W and the amplitude L of the waveform of the pulse of the photoelectric pulse wave. Accordingly, the normalized pulse-wave area $S_F$ is not influenced by the change of the heart rate, body temperature, or the like, of the subject, whereby the BP monitor apparatus 8 can obtain reliable monitor blood-pressure values VRBP.

Figure 6:
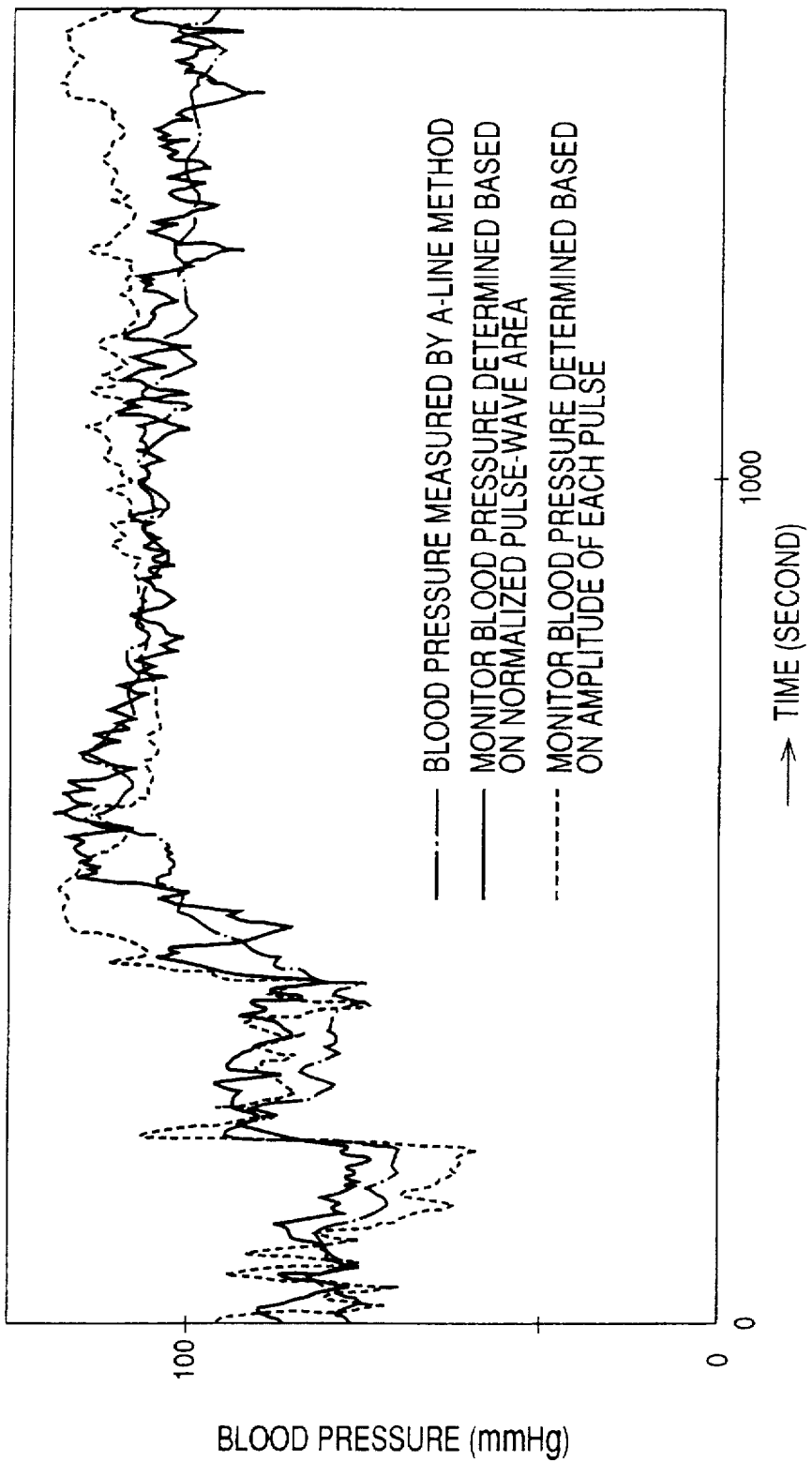
FIG. 6 is a view showing respective trend graphs of a monitor blood pressure VRBP estimated based on a normalized pulse-wave area $S_F$ by the apparatus of FIG. 1, a systolic blood pressure SBP measured by a A-LINE direct method and a monitor blood pressure AMPBP estimated based on an amplitude AMP of each pulse of the photoelectric pulse wave.
Figure 7:
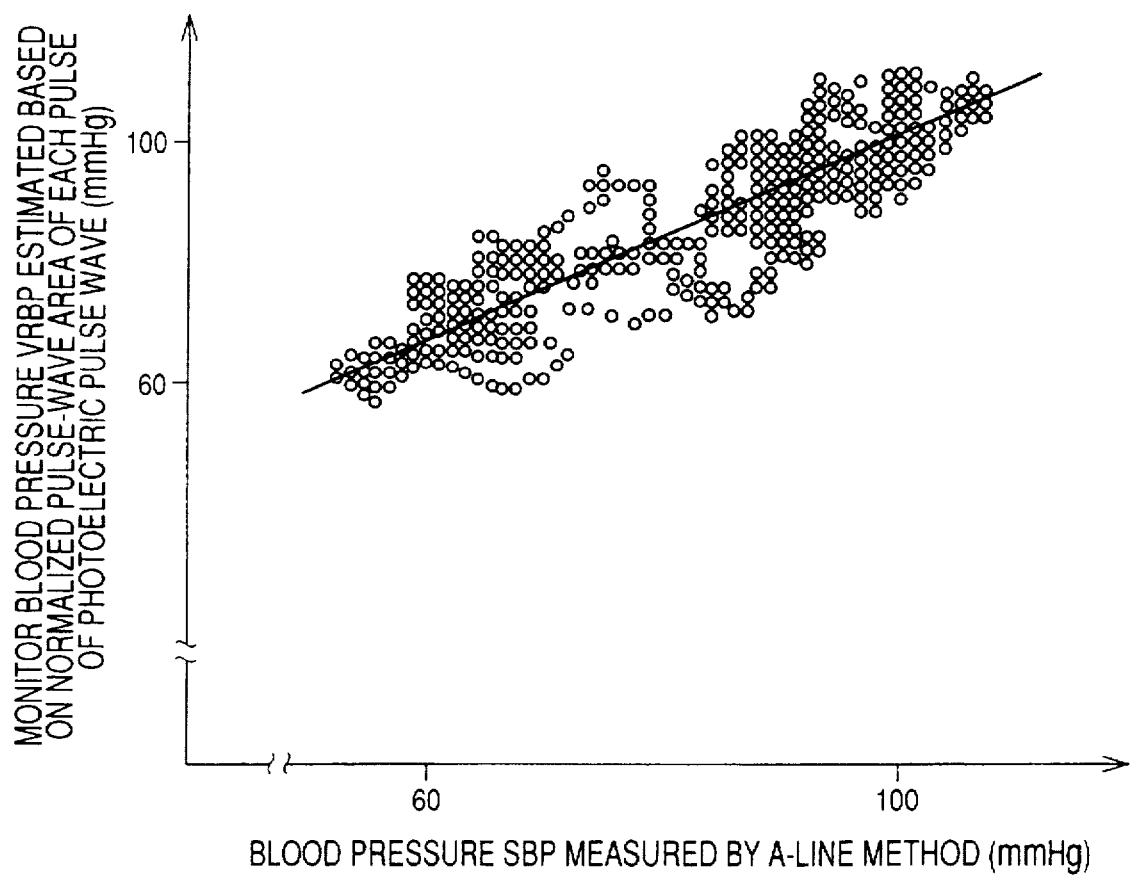
FIG. 7 is a view showing a correlation between the monitor blood pressure values VRBP and the systolic blood pressure values SBP.
Figure 8:
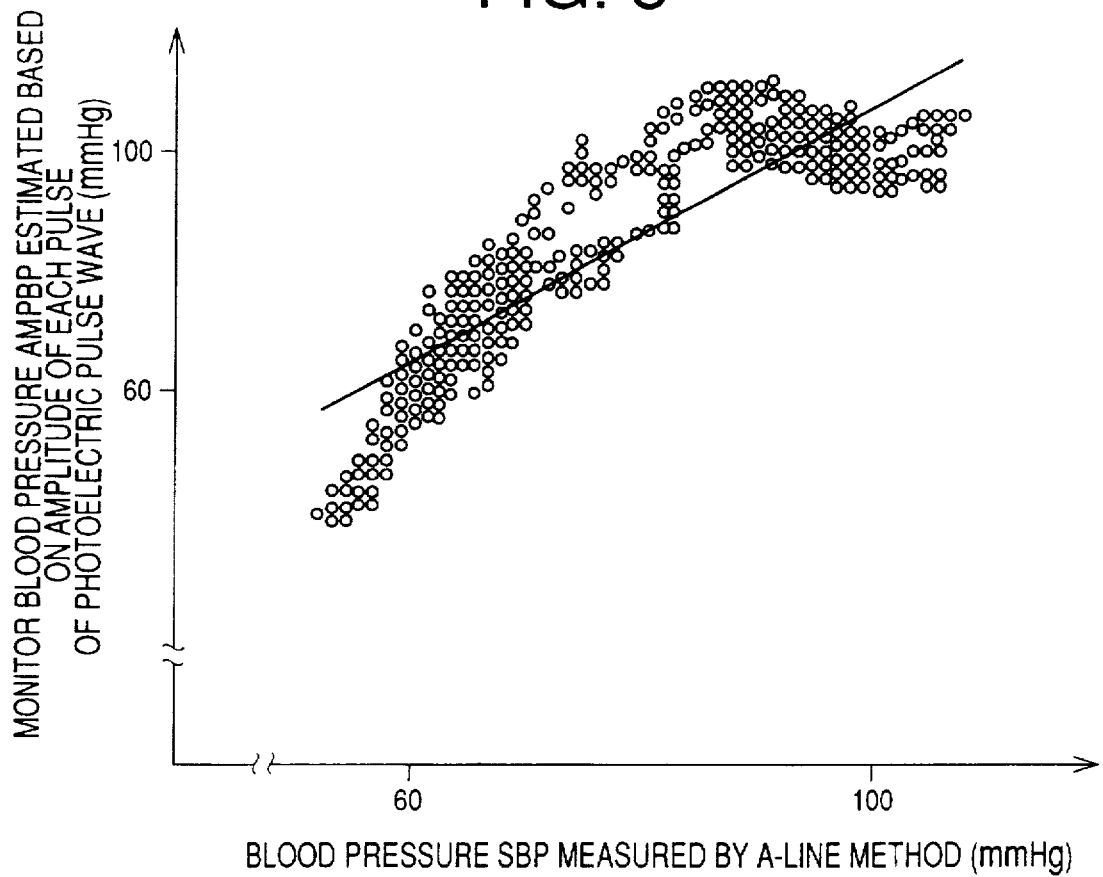
FIG. 8 is a view showing a correlation between the monitor blood pressure values AMPBP and the systolic blood pressure values SBP.

FIG. 6 shows respective trend graphs of the monitor blood pressure VRBP (systolic blood pressure), a blood pressure SBP (systolic blood pressure) and another monitor blood pressure AMPBP (systolic blood pressure), which are indicated at solid line, one-dot chain line and broken line, respectively. The monitor blood-pressure values VRBP are determined or estimated based on the normalized pulse-wave area values $S_F$. The blood pressure values SBP are measured by an A-LINE method in which a pressure in a blood vessel of the subject is directly measured by utilizing a catheter. The monitor blood-pressure values AMPBP are determined or estimated based on respective amplitudes AMP of heartbeat-synchronous pulses of the photoelectric pulse wave, according to a predetermined relationship between pulse amplitude and blood pressure. FIG. 7 shows a correlation between monitor blood pressure VRBP and blood pressure SBP. FIG. 8 shows a correlation between monitor blood pressure AMPBP and blood pressure BP.

As is apparent from FIG. 6, the monitor blood pressure VRBP estimated based on the normalized pulse-wave area $S_F$ faithfully follows the blood pressure SBP measured by the A-LINE method, in comparison with the monitor blood pressure AMPBP estimated based on the pulse amplitude AMP. That is, the monitor blood pressure VRBP enjoys a higher correlation with the true blood pressure SBP, than the monitor blood pressure AMPBP, and done not change so largely as time passes. Accordingly, in the BP monitor apparatus 8 which determines the monitor blood pressure VRBP based on the normalized pulse-wave area $S_F$, the need to update the pulse wave area-blood pressure relationship by operating the blood pressure measuring device 70 is minimized.

In FIG. 7, data points indicative of the correlation between the monitor blood pressure VRBP and the blood pressure SBP are more normally distributed on the upper and lower side of the straight line (indicated at solid line) representative of the correlation coefficient, in comparison with those of FIG. 8 which shows the correlation between the monitor blood pressure AMPBP and the blood pressure SBP. Thus, in a wider pressure range, a blood pressure of the subject can be estimated with high accuracy. That is, the BP monitor apparatus 8 can obtain monitor blood-pressure values VRBP with high reliability.

In the above described embodiment, the trend graph of the monitor blood-pressure values VRBP successively determined by the monitor blood pressure determining means 78 (Step SA9) is indicated on the display device 36, so that a doctor can easily recognize any change of the blood-pressure values and can accurately diagnose the patient.

Next, there will be described another embodiment according to the present invention. Hereinafter, the same parts as those of the prior embodiment will be denoted by the same reference numerals and the description thereof is omitted.

Figure 9:
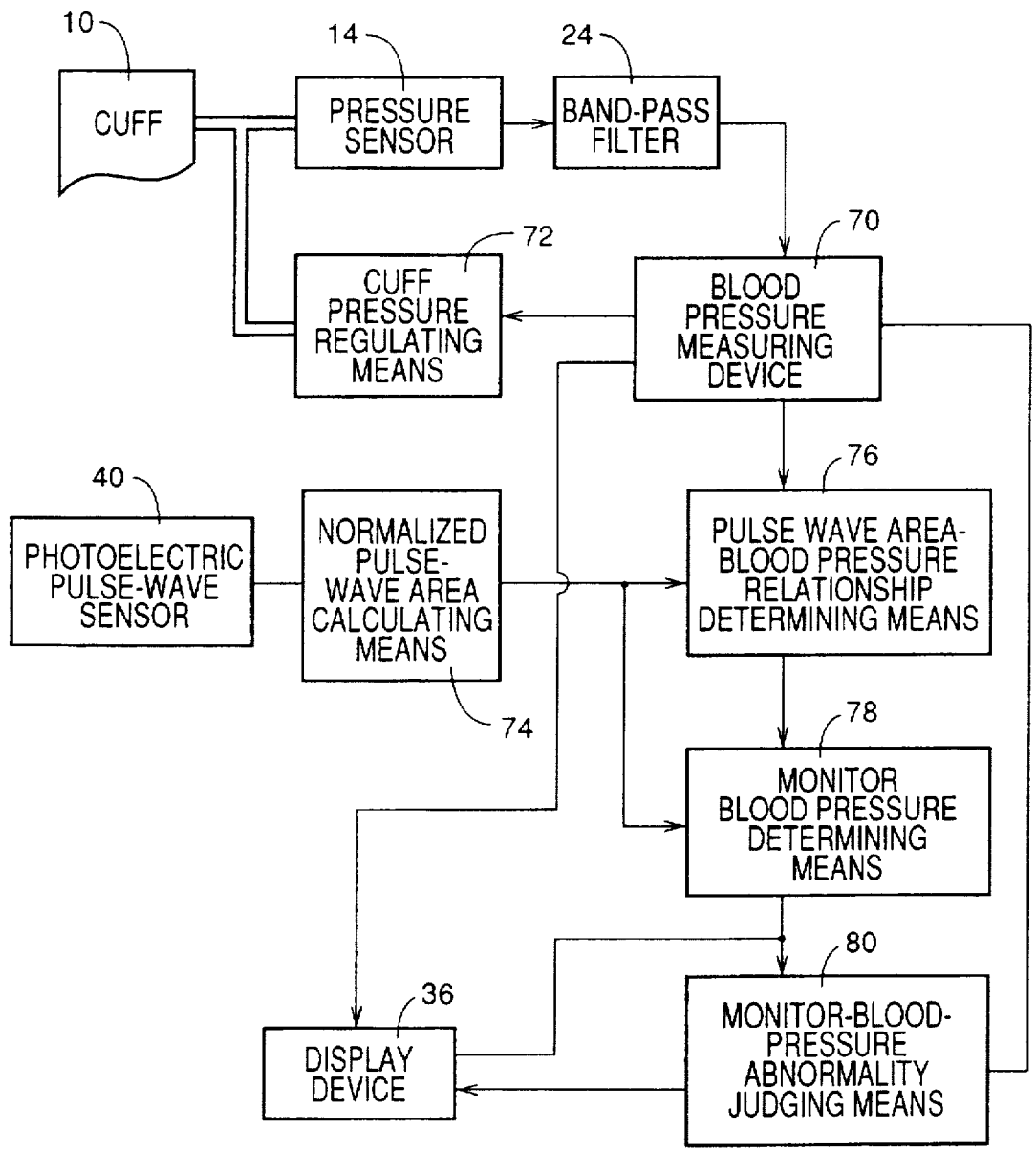
FIG. 9 is a block diagram for illustrating essential functions of an electronic control device of a blood pressure monitor apparatus according to a second embodiment of the present invention.
Figure 10:
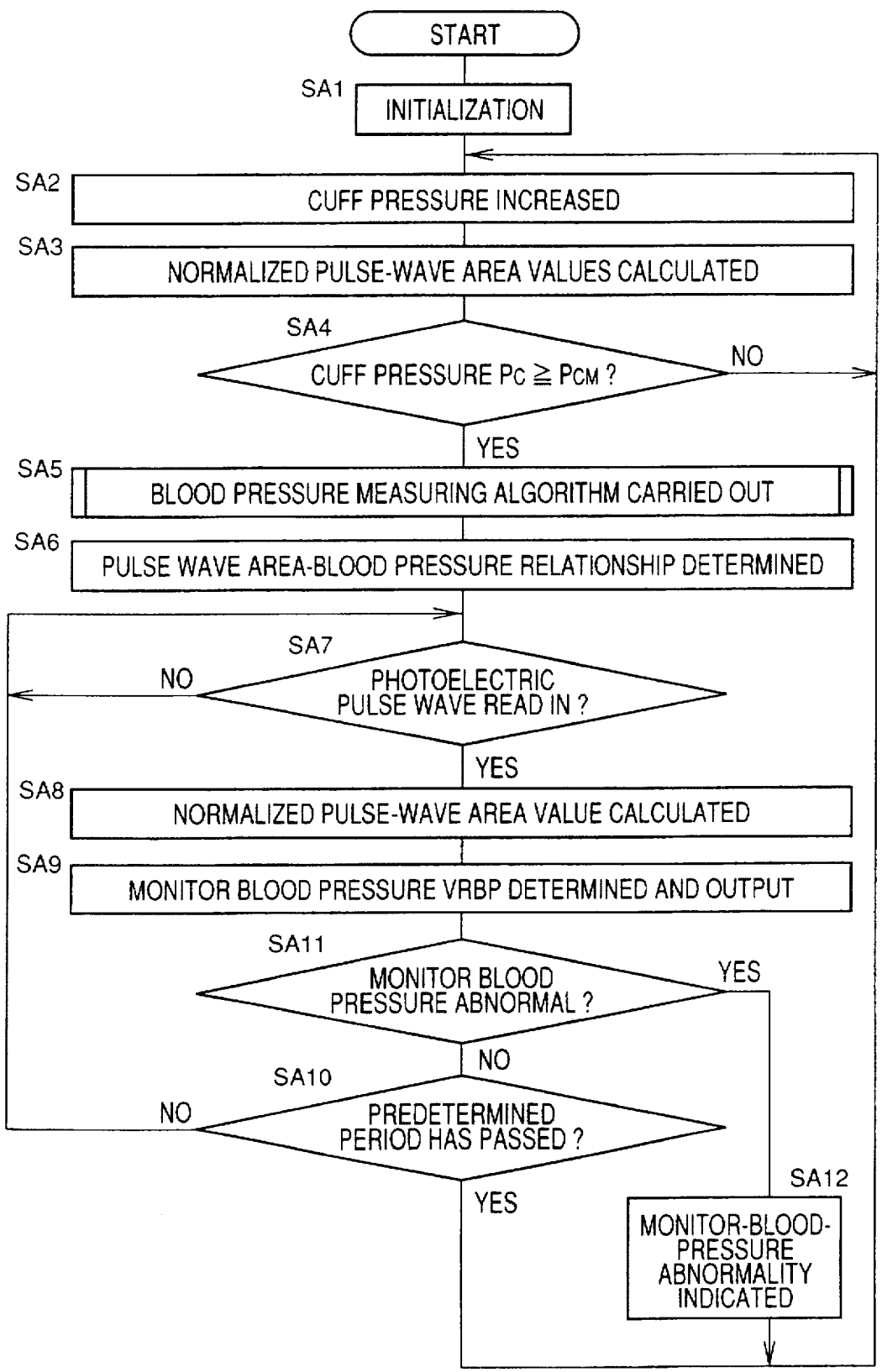
FIG. 10 is a flow chart representing the operation of the electronic control device of the apparatus of FIG. 9.

FIG. 9 is a block diagram for explaining essential functions of an electronic control device 28 of a BP monitor apparatus to which the second embodiment is applied and which has the same hardware construction as that of the prior embodiment shown in FIG. 1. FIG. 10 is a flow chart representing a control program according to which the apparatus of FIG. 9 is operated. The electronic control device 28 shown in FIG. 9 is different from the electronic control device 28 shown in FIG. 2 in that the former device 28 additionally includes a monitor-blood-pressure abnormality judging means 80 and Steps SA11 and SA12.

In FIG. 9, the monitor-blood-pressure abnormality judging means 80 judges whether each of the monitor blood-pressure values successively determined by the monitor blood pressure determining means 78 does not fall in a predetermined reference range, and controls, when a negative judgment is made, the blood pressure measuring device 70 to start a blood pressure measuring operation for determining a new pulse wave area-blood pressure relationship (VRBP=$\alpha \cdot S_F + \beta$), and the display device 36 to indicate that the negative judgment is made. The reference range is a criterion for judging that the blood pressure of the subject has been abnormally changed. For example, in the case where systolic blood pressure values are determined as the monitor blood-pressure values VRBP, the reference range may be the range of 90 to 180 mmHg.

In the flow chart of FIG. 10, at Step SA11, the CPU 30 judges whether the monitor blood-pressure value VRBP determined at Step SA9 is abnormal, i.e., does not fall in the reference range. If a negative judgment is made at Step SA11, the control of the CPU 30 goes to Step SA10 to judge whether or not the predetermined period has passed in the same manner as carried out in the prior embodiment. If a positive judgment is made at Step SA11, the control of the CPU 30 goes to Step SA12 to control the display device 36 to indicate that the abnormal blood pressure value has been detected. Then, the control of the CPU 30 goes back to Step SA2 to determine a new pulse wave area-blood pressure relationship (VRBP=$\alpha \cdot S_F + \beta$).

In the above described embodiment, the photoelectric pulse-wave sensor 40 is employed, so that the apparatus 8 can monitor the blood pressure of the subject without any delay, based on the monitor blood-pressure value VRBP determined for each of heartbeat-synchronous pulses, whereby the same effects as those of the prior embodiment are obtained. Additionally, when the judgment that the monitor blood-pressure value does not fall in the reference range is made by the monitor-blood-pressure abnormality judging means 80 (Steps SA11 and SA12), a blood pressure measuring operation of the blood pressure measuring device 70 (Step SA5) is started and a new pulse wave area-blood pressure relationship (VRBP=$\alpha \cdot S_F + \beta$) is determined by the pulse wave area-blood pressure relationship determining means 76 (Step SA6). Thus, the BP monitor apparatus can automatically obtain a blood pressure value with higher reliability upon detection of the blood pressure abnormality, and the reliability of the monitor blood-pressure values obtained after the detection of the abnormality is raised.

Next, there will be described still another embodiment according to the present invention. Hereinafter, the same parts as those of the prior embodiments will be denoted by the same reference numerals and the description thereof is omitted.

Figure 11:
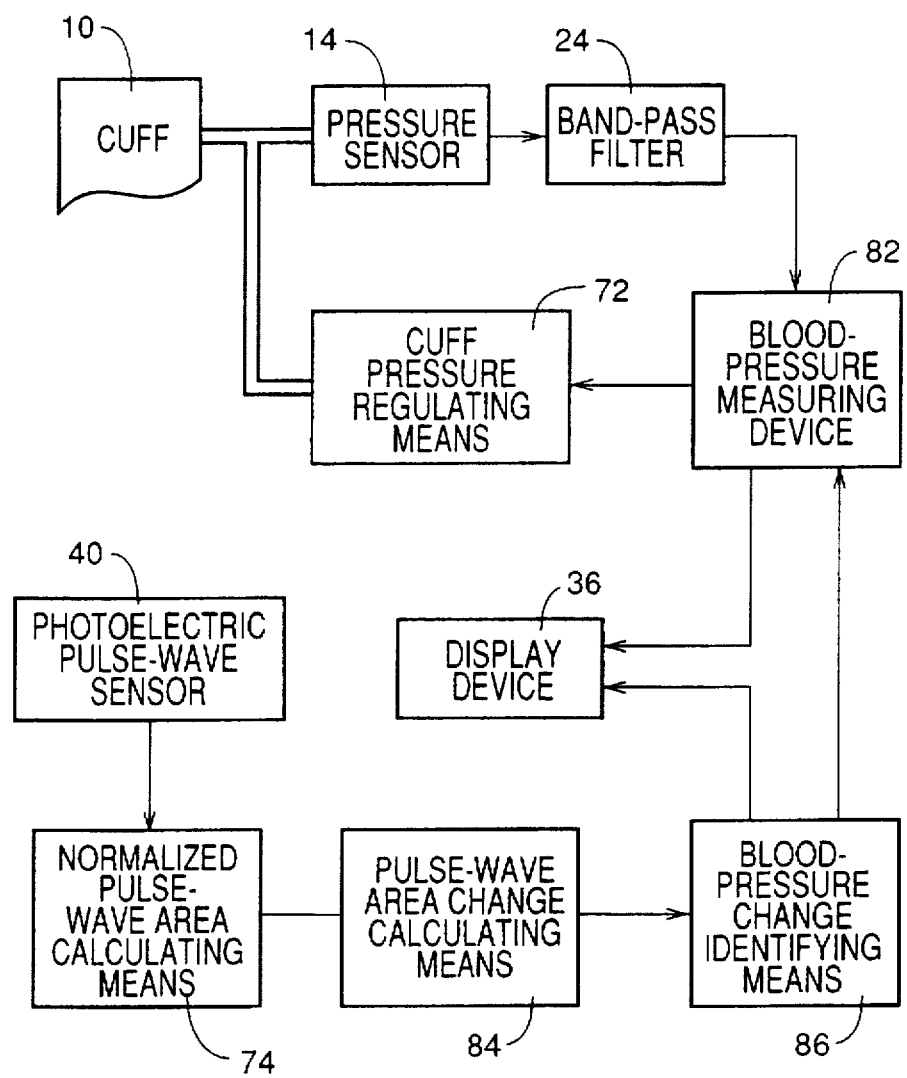
FIG. 11 is a block diagram for illustrating essential functions of an electronic control device of a blood pressure monitor apparatus according to a third embodiment of the present invention.
Figure 12:
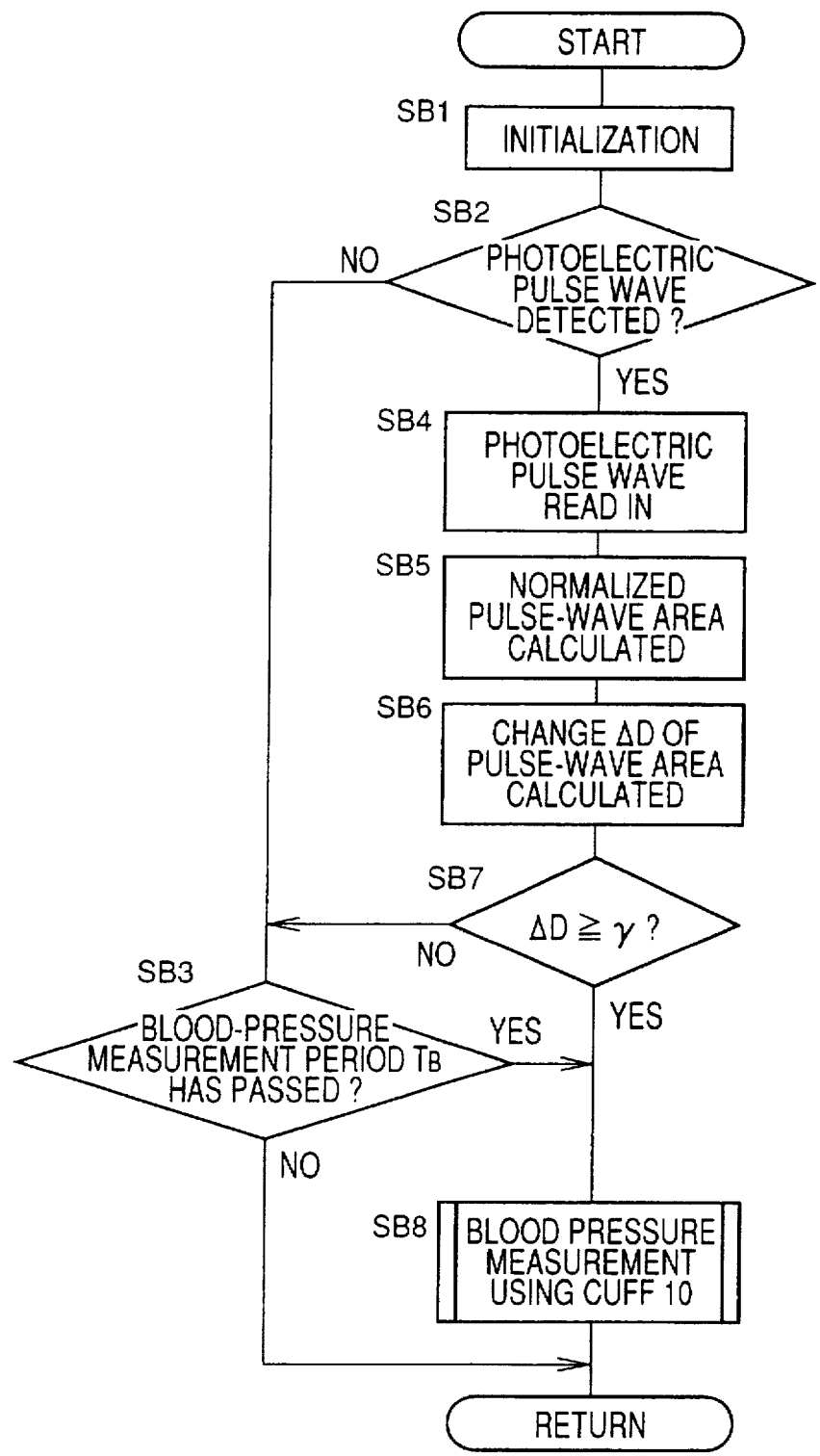
FIG. 12 is a flow chart representing the operation of the electronic control device of the apparatus of FIG. 11.

FIG. 11 is a block diagram for explaining essential functions of an electronic control device 28 of a BP monitor apparatus to which the third embodiment is applied and which has the same hardware construction as that of the first embodiment shown in FIG. 1. FIG. 12 is a flow chart representing a control program according to which the apparatus of FIG. 11 is operated. The electronic control device 28 shown in FIG. 11 is different from the electronic device 28 shown in FIG. 2 in that the former device 28 carries out a blood pressure monitor method different from that carried out by the latter device 28. More specifically, the BP monitor apparatus according to the third embodiment identifies an abnormal blood-pressure change of the subject, when a change $\Delta D$ of the normalized pulse-wave area values $S_F$ exceeds a reference value $\gamma$ while the blood pressure measurement using the cuff 10 is not carried out. When the change $\Delta D$ of the normalized pulse-wave area values exceeds the reference value $\gamma$, the apparatus starts a blood pressure measuring operation using the cuff 10.

In FIG. 11, a blood pressure measuring device 82 starts, at a predetermined period $T_B$, a blood pressure measuring operation using the cuff 10 in the same manner as that in which the BP measuring device 70 does in the prior embodiments, and indicates the measured blood pressure values on the display device 36. A pulse-wave area change calculating means 84 calculates a change $\Delta D$ of the normalized pulse-wave area values $S_F$ successively calculated by the normalized pulse-wave area calculating means 74. The change $\Delta D$ may be a rate or amount of change of the current normalized pulse-wave area value $S_F$ from a moving average of the normalized pulse-wave area values $S_F$, or the normalized pulse-wave area value $S_F$ calculated in the prior blood pressure measurement of the blood pressure measuring device 82. A blood-pressure change identifying means 86 identifies an abnormal blood-pressure change of the subject when the change $\Delta D$ of the normalized pulse-wave area values $S_F$ is greater than the reference value $\gamma$. Upon identification of the abnormal blood-pressure change, the blood pressure change identifying means 86 controls the display device 36 to indicate the abnormal blood-pressure change, and controls the pressure measuring device 82 to start a blood pressure measuring operation. Thus, the blood-pressure change identifying means 86 functions as a blood pressure measurement starting means for starting a blood pressure measuring operation when the change $\Delta D$ of the normalized pulse-wave area values $S_F$ is greater than the reference value $\gamma$.

In FIG. 12, at Step SB1, the CPU 30 carries out an initializing operation in the same manner as carried out at Step SA1. Step SB1 is followed by Step SB2 to judge whether or not a photoelectric pulse wave has been detected. If a negative judgment is made at Step SB2, the control of the CPU 30 goes to Step SB3. At Step SB3, the CPU 30 judges whether or not the predetermined period $T_B$ has passed after the prior blood pressure measurement was carried out at Step SB8. For example, the period $T_B$ may be a relatively long period such as ten and several minutes to several tens of minutes. If a negative judgment is made at Step SB3, the present routine is terminated and the control of the CPU 30 goes back to Step SB1. If a positive judgment is made at Step SB3, the control of the CPU goes to Step SB8 to carry out a blood pressure measurement using the cuff 10 according to an oscillometric method, output the measured systolic and diastolic blood pressure values $BP_{SYS}$, $BP_{DIA}$, and terminate the present routine.

If a positive judgment is made at Step SB2, the control of the CPU 30 goes to Step SB4 to read in the photoelectric pulse wave detected by the photoelectric pulse-wave sensor 40. Step SB4 is followed by Step SB5 to calculate a normalized pulse-wave area $S_F$ in the same manner as carried out at Step SA8. Step SB5 corresponds to the pulse-wave area calculating means 74. Step SB5 is followed by Step SB6 to calculate a change $\Delta D$ of the normalized pulse-wave area value $S_F$. The change $\Delta D$ of the normalized pulse-wave area value $S_F$ may be an absolute value of an amount, $S_{Fi} - S_{FAV}$, or a rate, $(S_{Fi} - S_{FAV})/S_{FAV}$, of change of the normalized pulse-wave area value $S_F$ to a moving average $S_{FAV} [=(S_{Fi-n} + \ldots + S_{Fi-1} + S_{Fi})/(n+1)]$ of the normalized pulse-wave area values, or an amount, $S_F - S_{Fm}$, or a rate, $(S_F - S_{Fm})/S_{Fm}$, of change of the normalized pulse-wave area value $S_F$ from the normalized pulse-wave area value $S_{Fm}$ calculated in the prior blood pressure measurement.

Step SB6 corresponds to the pulse-wave area change calculating means 84.

Step SB6 is followed by Step SB7 to judge whether or not the change ΔD of the normalized pulse-wave area value $S_F$ is equal to or greater than the reference value γ. Step SB7 corresponds to the blood-pressure change identifying means 86. The reference value γ is experimentally obtained in advance as a criterion for identifying an abnormal blood-pressure change of the subject.

If a negative judgment is made at Step SB7, the control of the CPU 30 goes to Step SB3. If a positive judgment is made at Step SB7, the control of the CPU 30 goes to Step SB8. At Step SB8, the CPU 30 starts a blood pressure measuring operation and controls the display device 36 to indicate the abnormal blood-pressure change in characters or symbols together with the measured blood pressure value.

In the above described embodiment, the normalized pulse-wave area value $S_F$ is calculated by the normalized pulse-wave area calculating means 74 (Step SB5). A change ΔD of the normalized pulse-wave area values $S_F$ is calculated by the pulse-wave area change calculating means 84 (Step SB6). The abnormal blood-pressure change of the subject is identified by the blood-pressure change identifying means 86 (Step SB7), when the change ΔD of the normalized pulse-wave area value $S_F$ is greater than the reference value γ. Thus, the BP monitor apparatus can identify the abnormal blood-pressure change of the subject based on the change of the normalized pulse-wave area value $S_F$ calculated for each pulse of the photoelectric pulse wave. Accordingly, the present apparatus need not carry out the blood pressure measurements at an unnecessarily short interval for improving the accuracy of the blood pressure monitor operation, whereby the frequency of pressing of the cuff 10 is decreased and the distress of the subject is minimized. Additionally, the photoelectric pulse-wave sensor 40 can be easily worn on the body portion of the subject. Since the signal detected by the sensor 40 is not changed by the body movement of the subject or the like, the BP monitor apparatus can continue the blood pressure monitor operation with accuracy.

In the above described embodiment, the blood-pressure change identifying means 86 (Step SB7) controls the blood pressure measuring device 82 to start a blood pressure measuring operation upon identification of the abnormal blood-pressure change of the subject. Thus, when the abnormal blood-pressure change of the subject is identified by the blood-pressure change identifying means 86, the blood pressure measurement of the blood pressure measuring device 82 is carried out, so that the BP monitor apparatus can automatically obtain a blood pressure value with high reliability.

Figure 13:
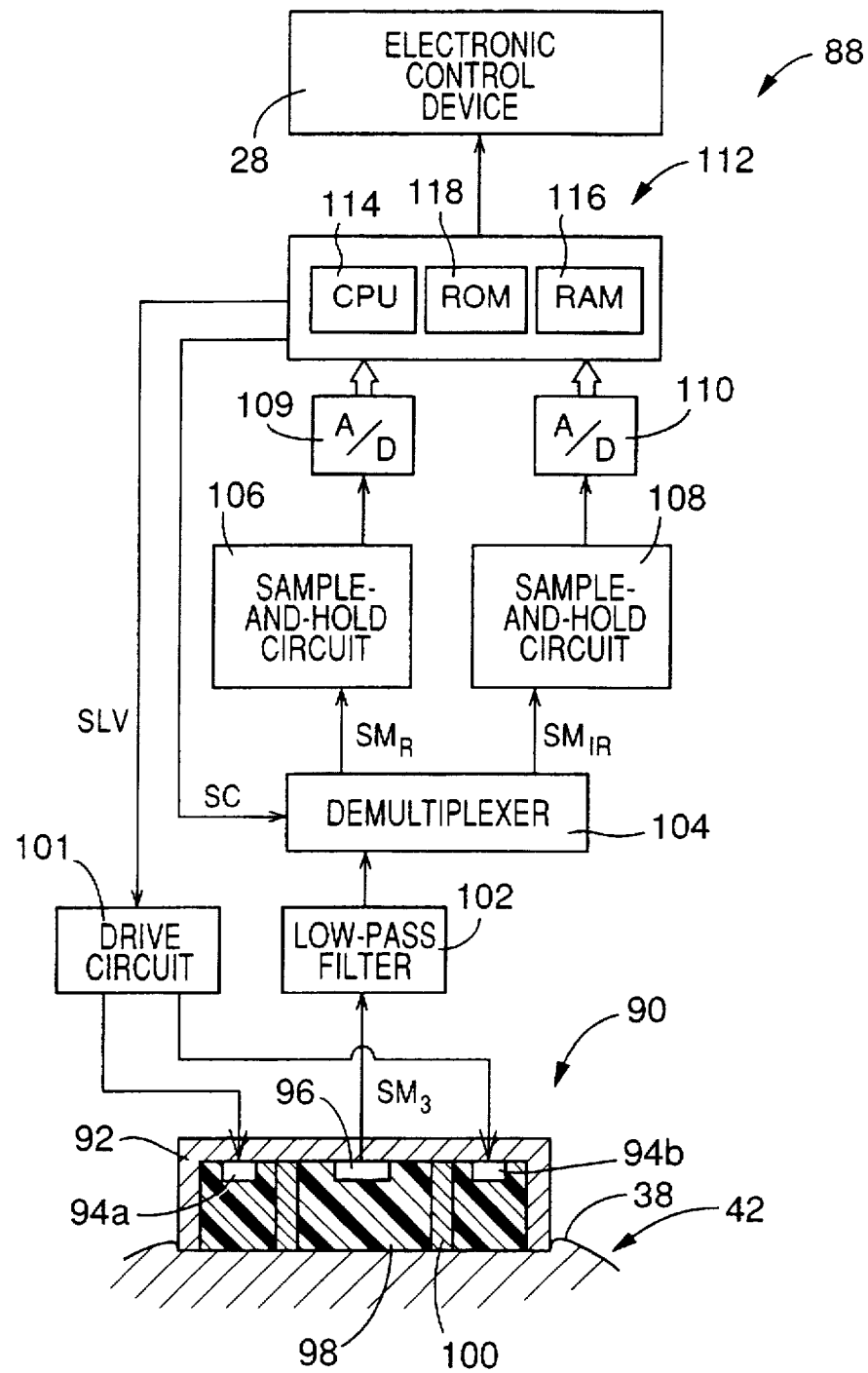
FIG. 13 is a diagrammatic view of a blood pressure monitor apparatus according to a fourth embodiment of the present invention, which includes, as a volume pulse-wave sensor, a photoelectric pulse wave detecting probe of a pulse oximeter.

FIG. 13 shows a BP monitor apparatus which employs a photoelectric pulse wave detecting probe 90 (hereinafter, referred to as the "probe") as part of a pulse oximeter 88 for measuring an oxygen saturation in blood of a living subject. The probe 90 functions as the volume pulse-wave sensor. The probe 90 is adapted to be set on a body surface 38 of the subject, e.g., a forehead of a patient, with the help of a band (not shown) such that the probe 90 closely contacts the body surface 38. The probe 90 includes a container-like housing 92 which opens in a certain direction, a first and a second group of light emitting elements 94a, 94b, such as LEDs (light emitting diodes), which are disposed on an outer peripheral portion of an inner bottom surface of the housing 92 (hereinafter, referred to as the light emitting elements 94 in the case where the first and second groups of light emitting elements 94a, 94b need not be discriminated from each other), a light receiving element 96, such as a photodiode or a phototransister, which is disposed on a central portion of the inner bottom surface of the housing 92, a transparent resin 98 which is integrally disposed in the housing 92 to cover the light emitting elements 94 and the light receiving element 96, and an annular shade member 100 which is disposed between the light emitting elements 94 and the light receiving element 96, for preventing the lights emitted toward the body surface 38 by the light emitting elements 94 and reflected from the body surface 38, from being received by the light receiving element 96.

The first and second groups of light emitting elements 94a, 94b emit a red light having about 660 nm wavelength and an infrared light having about 800 nm wavelength, respectively. The first and second light emitting elements 94a, 94b alternately emit the red and infrared lights at a predetermined frequency, according to a drive current supplied from a drive circuit 101. The lights emitted toward the body surface 38 by the light emitting elements 94 are reflected from a body tissue of the subject where a dense capillaries occur, and the reflected lights are received by the common light receiving element 96.

The light receiving element 96 outputs, through a low-pass filter 102, a photoelectric pulse-wave signal $SM_3$ representative of an amount of the received light. The light receiving element 96 is connected to the low-pass filter 102 via an amplifier or the like. The low-pass filter 102 eliminates, from the photoelectric pulse-wave signal $SM_3$ input thereto, noise having frequencies higher than that of a pulse wave, and outputs the noise-free signal $SM_3$, to a demultiplexer 104. The demultiplexer 104 is alternately switched according to signals supplied thereto from the electronic control device 28 in synchronism with the light emissions of the first and second light emitting element 94a, 94b. Thus, the demultiplexer 104 successively supplies, to an I/O port (not shown) of an electronic control device 112 of the pulse oximeter 88, an electric signal $SM_R$ representative of the red light through a sample-and-hold circuit 106 and an A/D converter 109, and an electric signal $SM_{IR}$ representative of the infrared light through a sample-and-hold circuit 108 and an A/D converter 110. The two sample-and-hold circuits 106, 108 hold the electric signals $SM_R$, $SM_{IR}$ input thereto, respectively, and do not output those current signals to the A/D converters 109, 110, before the prior signals $SM_R$, $SM_{IR}$ are completely converted by the A/D converters 109, 110, respectively. The electronic control device 112 is connected to a display device (not shown) so as to display the measured blood oxygen saturation.

The electronic control device 112 is provided by a microcomputer including a central processing unit (CPU) 114, a random access memory (RAM) 116 and a read only memory (ROM) 118. The electronic control device 112 mutually communicate information with the electronic control device 28. The CPU 114 performs a blood oxygen saturation measurement, by utilizing the temporary storage function of the RAM 116 according to the programs pre-stored in the ROM 118, calculates an oxygen saturation based on the electric signals $SM_R$, $SM_{IR}$, controls the display device to indicate the measured oxygen saturation, and outputs, as the volume pulse wave, the electric signal $SM_R$ or $SM_{IR}$ representative of a waveform similar to that shown in FIG. 4 to the electronic control device 28.

The blood oxygen saturation is determined based on an actual ratio $\{(V_{dR}-V_{SR})/(V_{dR}+V_{SR})\}/\{(V_{dIR}-V_{SIR})/(V_{dIR}+V_{SIR})\}$, according to a predetermined relationship between ratio $\{(V_{dR}-V_{SR})/(V_{dR}+V_{SR})\}/\{(V_{dIR}-V_{SIR})/(V_{dIR}+V_{SIR})\}$ and blood oxygen saturation. The blood oxygen saturation determining method is disclosed in U.S. Pat. No. 5,131,391. In the ratio $\{(V_{dR}-V_{SR})/(V_{dR}+V_{SR})\}/\{(V_{dIR}-V_{SIR})/(V_{dIR}+V_{SIR})\}$ the values $V_{dR}$, $V_{SR}$ respectively represent an upper and a lower peak value of a waveform of one pulse of the photoelectric pulse wave obtained from the red light, and the values $V_{dIR}$, $V_{SIR}$ respectively represent an upper and a lower peak value of a waveform of one pulse of the photoelectric pulse wave obtained from the infrared light. The values, $V_{dR}$, $V_{SR}$, $V_{dIR}$–$V_{SIR}$, respectively represent amplitudes of alternating current components of the respective photoelectric pulse waves obtained from the red and the infrared lights. The values, $V_{dR}+V_{SR}$, $V_{dIR}+V_{SIR}$, respectively represent double the respective amplitudes of direct current components of the respective photoelectric pulse waves obtained from the red and the infrared lights.

While the present invention has been described in its preferred embodiments by reference to the drawings, it is to be understood that the invention may otherwise be embodied.

While in the illustrated embodiments the photoelectric pulse-wave sensor 40 or the blood oxygen saturation detecting probe 90 which output the electric signals $SM_R$, $SM_{IR}$ are employed as the volume pulse-wave sensor, an impedance pulse-wave sensor which outputs an impedance pulse-wave signal may be employed. The impedance pulse-wave sensor includes at least two electrodes being set on different locations of a skin of a living subject at a predetermined interval, and outputs the impedance pulse-wave signal representing an instantaneous blood volume in a tissue of the skin located between the two electrodes.

In each of the illustrated embodiments shown in FIGS. 2, 9 and 11, a blood pressure of a living subject is monitored based on a normalized pulse-wave area value $SM_F$ successively calculated for each pulse of the photoelectric pulse wave. However, the blood pressure of the subject may be monitored, based on a normalized pulse-wave area value $SM_F$ calculated every second pulse of the photoelectric pulse wave, or at an interval such as several seconds to several tens of seconds.

In each of the illustrated embodiments, a blood pressure of a living subject is monitored based on a normalized pulse-wave area value $S_F$. However, in place of the normalized pulse-wave area value $S_F$, one of normalized first and second pulse-wave area values may be employed. The normalized first pulse-wave area value is calculated by normalizing a first pulse-wave area $S_1$ defined by the waveform of a pulse of the photoelectric pulse wave between a rising point and an upper peak point of the waveform shown in FIG. 4. The normalized second pulse-wave area is calculated by normalizing a second pulse-wave area $S_2$ which corresponds to the rest that the first pulse-wave area $S_1$ is taken away from the pulse-wave area S. Otherwise, for example, a normalized value I/W which is obtained by normalizing a width I between two points on the waveform which correspond to L·(⅔) may be employed. In short, the BP monitor apparatus according to the present invention may calculate a value relating to an area defined by a waveform of each of heartbeat-synchronous pulses of the volume pulse wave, or a value representative of a sharpness of an upper peak of the waveform of each pulse of the volume pulse wave.

In the above described first and second embodiments, the pulse wave area-blood pressure relationship determining means 76 (Step SA6) employs, as the relationship between pulse-wave area and blood pressure, the liner expression (VRBP=α·$S_F$+β). However, a quadratic or higher polynomial expression may be employed, and one or more correcting terms may be added if necessary.

In each of the above described embodiments, the blood pressure measuring devices 70, 82 measure a blood pressure value of a living subject based on a variation of the pulse wave produced while the cuff pressure $P_C$ is slowly decreased. However, the blood pressure measuring devices may measure a blood pressure value of the subject based on a variation of a pulse wave produced while the cuff pressure $P_C$ is slowly increased.

In each of the above described embodiments, the blood pressure measuring devices 70, 82 employ the so-called oscillometric method to measure a blood pressure value of a living subject based on a variation of a pressure pulse wave produced while the cuff pressure $P_C$ is changed. However, the blood pressure measuring devices may employ a so-called Korotokoff-sound method to determine a blood pressure value of the subject based on the pressing pressure of the cuff 10 at the time of occurrence or disappearance of Korotokoff-sounds.

It is to be understood that the present invention may be embodied with other changes and modifications that may occur to those skilled in the art without departing from the scope of the invention.

What is claimed is:

1. A blood pressure monitor apparatus comprising:

a blood pressure measuring device which includes a cuff adapted to be pressed on an artery of a living subject and measures a blood pressure value of the subject by changing a pressing pressure of the cuff;

a volume pulse wave detecting device which detects a volume pulse wave of the subject;

normalized pulse-wave area calculating means for successively calculating an area which is defined by a waveform of each of heartbeat-synchronous pulses of the volume pulse wave detected by said volume pulse wave detecting device and is normalized based on a period and an amplitude of said each pulse of the volume pulse wave;

pulse wave area-blood pressure relationship determining means for determining a relationship between pulse-wave area and blood pressure, based on a normalized pulse-wave area value calculated by said normalized pulse-wave area calculating means and a blood pressure value measured by said blood pressure measuring device, when said blood pressure value is measured; and monitor blood pressure determining means for successively determining a monitor blood-pressure value of the subject, based on each of normalized pulse-wave area values successively calculated by said normalized pulse-wave area calculating means, according to the pulse wave area-blood pressure relationship determined by said pulse wave area-blood pressure relationship determining means.

2. A blood pressure monitor apparatus according to claim 1, further comprising monitor-blood-pressure abnormality judging means for judging whether each of the monitor blood-pressure values successively determined by said monitor blood pressure determining means does not fall in a reference range, and controlling, when a negative judgment is made, said blood pressure measuring device to start a blood pressure measuring operation.

3. A blood pressure monitor apparatus according to claim 2, further comprising an indicating device which indicates a trend graph of the monitor blood-pressure values successively determined by said monitor blood pressure determining means.

4. A blood pressure monitor apparatus according to claim 3, wherein said indicating device comprises means for indicating that said negative judgment is made by said monitor-blood-pressure abnormality judging means.

5. A blood pressure monitor apparatus according to claim 1, wherein said volume pulse wave detecting device comprises a photoelectric pulse-wave sensor including a light-emitting and a light-receiving element, the light-emitting element adapted to emit, toward a skin of the subject, a light having a wavelength which can be reflected by hemoglobin present in blood of the skin, the light-receiving element adapted to receive the light scattered by the hemoglobin from the skin, said photoelectric pulse-wave sensor outputting a photoelectric pulse wave signal representing an instantaneous blood volume in capillaries of the skin.

6. A blood pressure monitor apparatus according to claim 1, wherein said volume pulse wave detecting device comprises an impedance pulse-wave sensor including at least two electrodes adapted to be set on different locations of a skin of the subject at a predetermined interval, said impedance pulse-wave sensor outputting an impedance pulse-wave signal representing an instantaneous blood volume in a tissue of the skin located between said two electrodes.

7. A blood pressure monitor apparatus including a blood pressure measuring device which includes a cuff being set on a body portion of a living subject and periodically measures a blood pressure value of the subject, based on a variation of a pulse wave produced while a pressing pressure of the cuff is changed, the blood pressure monitor apparatus comprising:

a volume pulse wave detecting device which detects a volume pulse wave of the subject;

normalized pulse-wave area calculating means for successively calculating an area which is defined by a waveform of each of heartbeat-synchronous pulses of the volume pulse wave detected by said volume pulse wave detecting device and is normalized based on a period and an amplitude of said each pulse of the volume pulse wave;

pulse-wave area change calculating means for calculating a change of the normalized pulse-wave area values successively calculated by said normalized pulse-wave area calculating means; and blood-pressure change identifying means for identifying an abnormal blood-pressure change of the subject when the change of the normalized pulse-wave area values is greater than a reference value.

8. A blood pressure monitor apparatus according to claim 7, wherein said blood-pressure change identifying means comprises means for controlling said blood pressure measuring device to start a blood pressure measuring operation upon identification of the abnormal blood-pressure change.

9. A blood pressure monitor apparatus according to claim 7, further comprising an indicating device which indicates the abnormal blood-pressure change of the subject upon identification of the abnormal blood-pressure change.

10. A blood pressure monitor apparatus according to claim 7, wherein said volume pulse wave detecting device comprises a photoelectric pulse-wave sensor including a light-emitting and a light-receiving element, the light-emitting element adapted to emit, toward a skin of the subject, a light having a wavelength which can be reflected by hemoglobin present in blood of the skin, the light-receiving element adapted to receive the light scattered by the hemoglobin from the skin, said photoelectric pulse-wave sensor outputting a photoelectric pulse wave signal representing an instantaneous blood volume in capillaries of the skin.

11. A blood pressure monitor apparatus according to claim 7, wherein said volume pulse wave detecting device comprises an impedance pulse-wave sensor including at least two electrodes adapted to be set on different locations of a skin of the subject at a predetermined interval, said impedance pulse-wave sensor outputting an impedance pulse-wave signal representing an instantaneous blood volume in a tissue of the skin located between said two electrodes.

* * * * *